United States Patent
Guala

(10) Patent No.: US 8,162,006 B2
(45) Date of Patent: Apr. 24, 2012

(54) ONE-WAY VALVE FOR MEDICAL INFUSION LINES AND THE LIKE

(75) Inventor: Gianni Guala, Turin (IT)

(73) Assignee: Industrie Borla S.p.A., Moncalieri (Torino) (IT)

( * ) Notice: Subject to any disclaimer, the term of this patent is extended or adjusted under 35 U.S.C. 154(b) by 632 days.

(21) Appl. No.: 12/015,170

(22) Filed: Jan. 16, 2008

(65) Prior Publication Data

US 2008/0169444 A1  Jul. 17, 2008

(30) Foreign Application Priority Data

Jan. 17, 2007  (IT) .............................. TO2007A0023

(51) Int. Cl.
*F16K 15/14* (2006.01)
(52) U.S. Cl. ..................... 137/843; 137/512.15; 604/247
(58) Field of Classification Search .................. 137/843, 137/859, 852, 512.15; 604/247
See application file for complete search history.

(56) References Cited

U.S. PATENT DOCUMENTS

| | | | |
|---|---|---|---|
| 4,958,661 A * | 9/1990 | Holtermann et al. ......... | 137/843 |
| 6,390,120 B1 * | 5/2002 | Guala ...................... | 137/512.15 |
| 6,409,707 B1 * | 6/2002 | Guala .......................... | 604/247 |

FOREIGN PATENT DOCUMENTS

| | | |
|---|---|---|
| DE | 195 45 421 A1 | 6/1997 |
| DE | 195 45 421 C2 | 6/1997 |
| EP | 0 791 371 B1 | 7/1999 |
| EP | 1 093 828 A2 | 4/2001 |
| EP | 1 093 828 A3 | 4/2001 |
| EP | 1 099 457 A2 | 5/2001 |
| EP | 1 099 457 A3 | 5/2001 |
| EP | 1099456 A1 | 5/2001 |
| EP | 1 093 828 B1 | 3/2003 |
| EP | 1 099 457 B1 | 9/2003 |

OTHER PUBLICATIONS

European Search Report for corresponding EP Application No. 07123017 dated Apr. 16, 2008.

* cited by examiner

*Primary Examiner* — Kevin Lee
*Assistant Examiner* — Macade Brown
(74) *Attorney, Agent, or Firm* — Heslin Rothenberg Farley & Mesiti P.C.; Victor A. Cardona, Esq.

(57) ABSTRACT

A check valve for medical infusion lines and the like, includes a diaphragm made of elastic material set between a first tubular connector and a second tubular connector. The diaphragm includes an end wall of a cup-shaped element, having an outer peripheral edge of which is normally pressed in seal contact against an annular valve seat with a conical surface of the first tubular connector under an axial thrust exerted by a side wall of the cup-shaped element. A free edge of the side wall of the cup-shaped element is set resting against a transverse surface of the second tubular connector only in regions corresponding to angular portions of the latter separated by non-resting angular portions.

16 Claims, 4 Drawing Sheets

ONE-WAY VALVE FOR MEDICAL INFUSION LINES AND THE LIKE

CROSS REFERENCE TO RELATED APPLICATIONS

This application claims priority from Italian patent application No. TO 2007 A 000023, filed on Jan. 17, 2007, the entire disclosure of which is incorporated herein by reference.

FIELD OF THE INVENTION

The present invention relates to one-way valves for medical infusion lines and the like, of the type generally comprising a first tubular element and a second tubular element, which define, respectively, a passage upstream and a passage downstream, which are coaxial to one another and set transversely between which is a diaphragm made of elastically deformable material, which co-operates in a fluid-tight way with the annular valve seat of the first tubular element to keep the valve normally closed. A predetermined pressure of fluid in the passage upstream brings about a displacement or an elastic deformation of the diaphragm and consequent opening of the valve, i.e., opening of the communication between the passage upstream and the passage downstream through channels formed in the two tubular elements.

Valves of the above sort are used, for example, as check valves, which are purposely designed so as to open when the pressure in the passage upstream is higher than a predetermined, relatively modest, threshold value and then to reclose promptly so as to prevent, with the maximum degree of safety, any reflux from the passage downstream to the passage upstream as soon as the pressure in the latter drops back below the threshold value, or else in the case of an albeit minimal overpressure within the passage downstream.

STATE OF THE PRIOR ART

German patent No. DE-C-19545421 filed in the name of Filtertek describes a check valve of the above sort expressly designed for operating in a range of pressures comprised between 0.1 and 0.02 bar. The diaphragm of the valve is constituted by a disk obtained by dinking from a silicone ribbon and the circumferencial edge of which is gripped between the two tubular elements of the valve. The disk is axially pre-loaded so that it rests at the front against the valve seat, defined by an axial annular projection of the first tubular element, and can be axially moved away therefrom when the pressure in the passage upstream falls within the range mentioned above.

A valve of the type referred to above, however simple and inexpensive thanks to the elementary shape of its diaphragm and to the simple process of production thereof by means of dinking, does not appear to be able to guarantee the necessary sensitivity and promptness for pressure values lower than the minimum one (0.02 bar) for which it is expressly designed.

In order to solve the above problem, and in particular to provide a check valve suitable for operating with the maximum safety and reliability with pressures in the passage upstream even markedly lower than 0.02 bar, the present applicant has proposed in his own European patent No. EP-B-1099457 a solution in which the diaphragm is constituted by the end wall of a particular cup-shaped element, obtained by injection moulding of silicone. Said end wall of the cup-shaped element has centrally an annular projection, which defines a seal lip co-operating at the front with the annular valve seat of the first tubular element, under the action of an axial preloading applied by the side wall of the cup-shaped element.

Even though this solution is constructionally more complex and hence more costly than the solution according to the document No. DE-C-19545421, it has in practice proven perfectly capable of achieving the desired effects.

On the other hand, the present applicant has proposed in European Patent No. EP-B-1093828 a similar valve, expressly designed, however, for use as anti-siphon valve, i.e., for medical applications with pressures in the passage upstream typically comprised between 1 and 5 psi (from approximately 0.07 to 0.35 bar). In this valve, the annular valve seat is defined by a wall with conical surface of the first tubular element, diverging towards the second tubular element, and also in this case the diaphragm is constituted by the end wall of a cup-shaped element, which, however, is pressed in seal contact against the annular seat with conical surface in a region corresponding to its own outer peripheral edge, also in this case under the axial thrust exerted by the side wall of the cup-shaped element. In operation, the pressure of fluid at the values indicated above in the passage upstream produces an axial displacement of the end wall of the cup-shaped element in the direction of the second tubular element, as a result of which the corresponding outer peripheral edge contracts radially moving away from the annular valve seat with a radial component.

This operation, which guarantees a surprising promptness and immediacy of opening of the valve, is in principle similar to what is described in European Patent No. EP-B-0791371, which is also in the name of the present applicant, with reference to a medical connector with protection valve that can be activated via a luer-lock connector.

SUMMARY OF THE INVENTION

The object of the present invention is to improve further the functional characteristics of the check valve according to European Patent No. EP-B-1099457, exploiting the concept of the anti-siphon valve according to European Patent No. EP-1093828 so as to enable application thereof at operating pressures even markedly below 0.02 bar.

With a view to achieving the above purpose, the subject of the invention is a one-way valve in compliance to what is claimed in the preamble of Claim 1, and generally corresponding to the anti-siphon valve according to the document No. EP-B-1093828, the primary characteristic of which lies in the fact that the free edge of the side wall of the cup-shaped element is set resting upon the grooved transverse surface of the second tubular element only in regions corresponding to angular portions separated by angular non-resting portions.

Thanks to this arrangement, the side wall of the cup-shaped element has an elastic compliance that is substantially higher than in the case where, as in the anti-siphon valve according to the document No. EP-B-1093828, its free edge is resting completely. This enables advantageous exploitation of the operating principle of the anti-siphon valve according to the document No. EP-B-1093828 for the applications typical of a medical check valve, i.e., with opening pressures even markedly below 0.02 bar.

According to a preferred of embodiment of the invention, the grooved transverse surface of the second tubular element has an array of radial channels separated from one another by alternately raised and sunken sectors. Said sectors define, respectively, the angular resting portions and the angular non-resting portions of the free edge of the side wall of the cup-shaped element.

The invention moreover envisages particular arrangements in relation to the structure and conformation of the cup-shaped element designed to improve further operation thereof, particularly in terms of promptness of opening and reclosing of the valve.

BRIEF DESCRIPTION OF THE DRAWINGS

The invention will now be described in detail with reference to the annexed plates of drawings, which are provided purely by of way of non-limiting example, and in which.

DETAILED DESCRIPTION OF THE INVENTION

Figure 1:
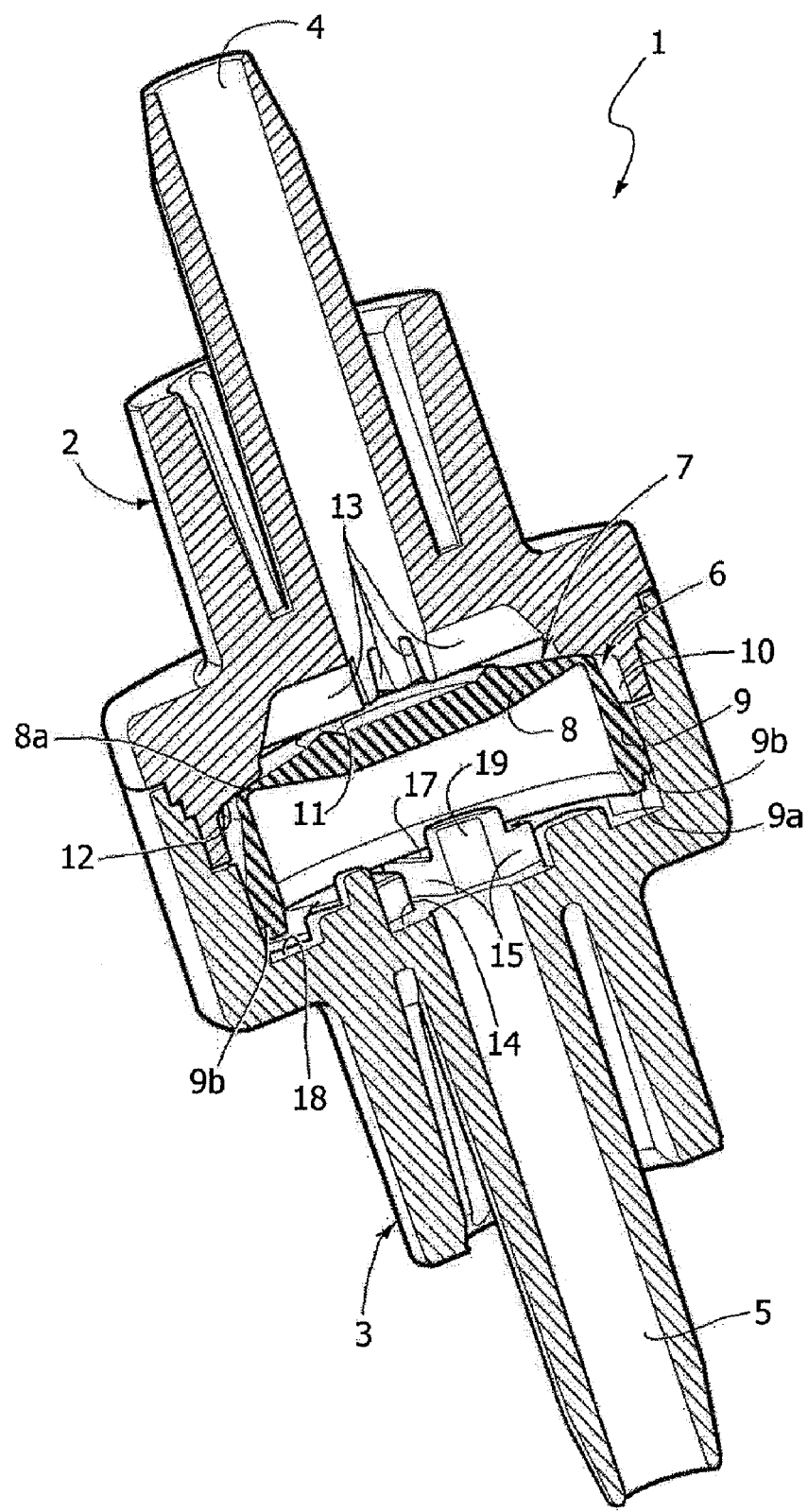
FIG. 1 is a schematic view in axial cross section of a check valve according to the invention.

With reference to the drawings, the number 1 designates as a whole an axial union for tube-tube connection for medical lines for infusion, transfusion and the like. It should at once be noted that the union could also be arranged for luer-tube connections or else tube-luer connections or luer-luer connections or any other type of connection.

The union 1 comprises, in a way in itself generally known, a first tubular connector 2 and a second tubular connector 3 both normally made of a suitable moulded thermoplastic material, for example polycarbonate or similar materials, and joined axially in a permanent way to one another, for example, via ultrasound welding or else gluing, or equivalent systems.

The first and second tubular connectors 2, 3 define, respectively, a passage upstream or inlet passage 4 and a passage downstream or outlet passage 5, which can be connected to respective sections of piping of a medical infusion line or the like.

Set between the passage upstream 4 and the passage downstream 5 is a check valve, designated as a whole by 6.

Figure 2:
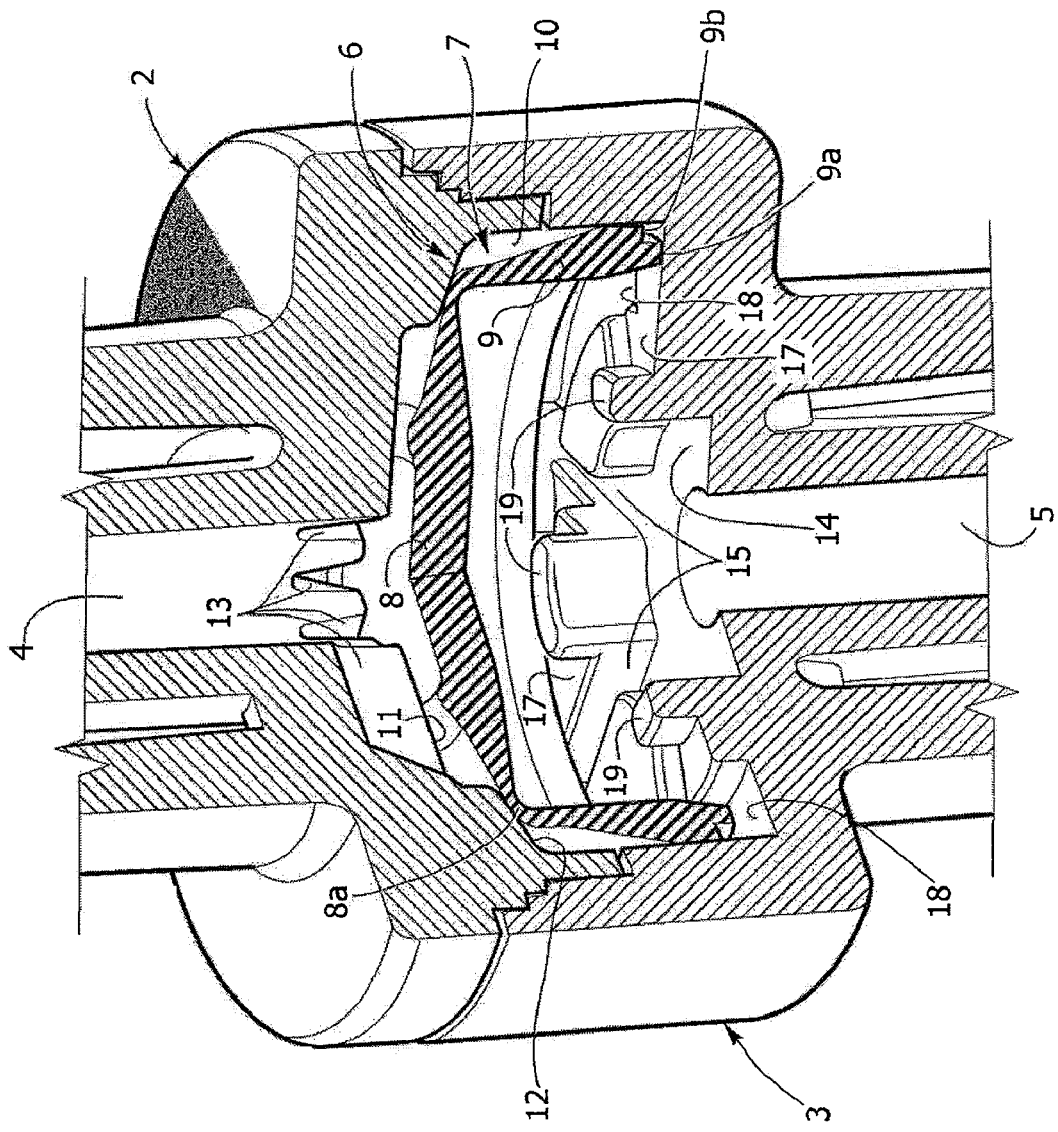
FIG. 2 is a view similar to that of FIG. 1, sectioned according to a different plane, partial and at an enlarged scale, of the check valve according to the invention.
Figure 3:
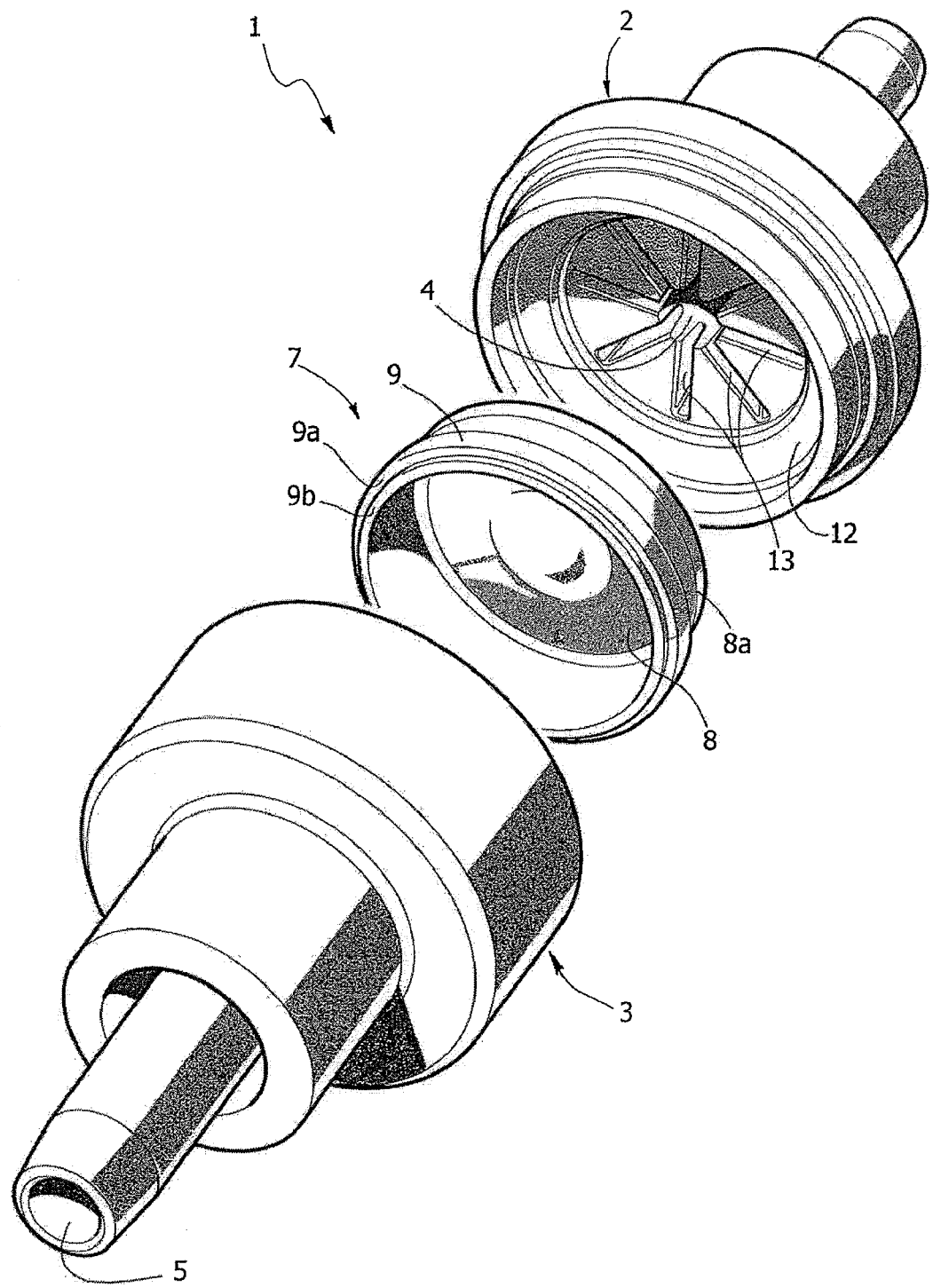
FIG. 3 is an exploded perspective view, from beneath, of the valve.
Figure 4:
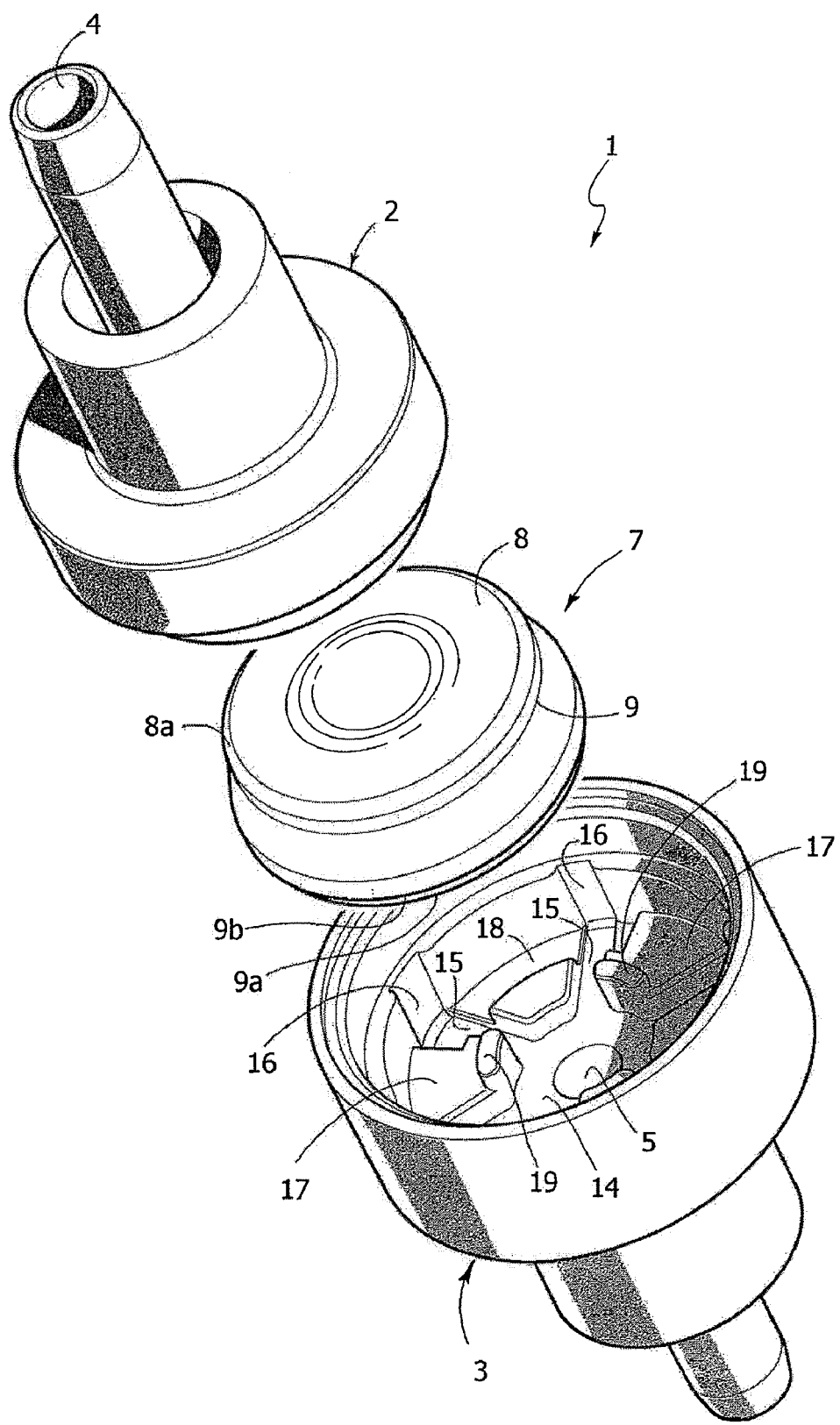
FIG. 4 is an exploded perspective view, from above, of the valve.

The check valve 6 basically comprises an elastic open/close element constituted by a cup-shaped element 7, represented in greater detail in FIGS. 3 and 4, which in FIGS. 1 and 2 is illustrated in its resting condition corresponding to closing of the valve 6. Said cup-shaped element 7 comprises a circular end wall 8, plane or more conveniently slightly convex, and a skirt or side wall 9 of a cylindrical shape, more conveniently with conical external surface diverging on the side opposite to the end wall 8.

As may be seen more clearly in FIGS. 1 and 2, the end wall 8 preferably has a variable thickness, greater in its central part and progressively decreasing towards its circumferencial edge designated by 8a. The circumferencial edge 8a can in turn present a reduced thickness, deriving from the presence of an external perimetral groove 9b.

Also the side wall 9 has a variable thickness progressively increasing towards its free edge 9a, i.e., the edge opposite to the end wall 8.

With a structure of the above sort, the area of connection between the side wall 9 and the circumferencial edge 8a of the end wall 8 has a minimum thickness that is considerably smaller than the maximum thickness of the side wall 9.

The circumferencial edge 8a of the end wall 8 conveniently has a rounded profile.

The cup-shaped element 7 is normally made of a single piece of an injection-moulded soft elastomeric material, in particular liquid silicone or other rubber.

To return to FIGS. 1 and 2, the cup-shaped element 7 is inserted in a chamber 10 defined between the first tubular element 2 and the second tubular element 3, coaxially to said elements.

The chamber 10 is axially delimited on one side by a transverse wall 11 of the first tubular element 2, onto which the inlet passage 4 gives out and which is delimited on the outside by a conical circumferencial surface 12 diverging towards the second tubular element 3, which defines an annular valve seat. Between the inlet passage 4 and the annular valve seat 12, the wall 11 has an array of projections or else grooves 13 facing the end wall 8 of the cup-shaped element 7, which in the undeformed condition of the latter is set axially at a distance from the wall 11.

On the opposite side, the chamber 10 is delimited by a transverse wall 14 of the second tubular connector 3, in a central area of which the outlet passage 5 gives out. The wall 14 is formed with an array of radial channels 15, which communicate on one side with the outlet passage 5 and on the opposite side with respective axial channels 16 formed in the wall of the second tubular element 3 and facing the external surface of the side wall 9 of the cup-shaped element 7.

Said cup-shaped element 7 is housed coaxially within the chamber 10, with its end wall 8 facing, like a transverse diaphragm, the inlet passage 4 and with its side wall 9 facing, as has been said, the axial channels 16. The free edge 9a of the side wall 9 rests on the transverse wall 14 of the second tubular element 3. According to the primary characteristic of the invention, it rests in a non-continuous way, in the sense that the free edge 9a is set resting upon the transverse wall 14 only in areas corresponding to angular portions separated by angular non-resting portions. This is obtained thanks to the fact that the radial channels 15 of the transverse wall 14 are separated from one another by sectors (in the example illustrated six in number, angularly set at the same distances apart from one another) that are alternately axially raised 17 and axially sunken 18. The free edge 9a is in contact with the raised sectors 17, whilst it is set at a distance from the sunken sectors 18, and is hence free in said areas.

The three raised sectors 17 are formed at the respective ends radially internal with respective axial projections 19, contained within the side wall 9 of the cup-shaped element 7 and projecting towards the end wall 8. Similar projections can possibly be provided also at the ends of the two sunken sectors 18.

In the closing condition of the valve 6 represented in FIG. 1, the external circumferencial edge 8a of the end wall 8 rests against the valve seat with conical surface 12 of the first tubular element 2. The arrangement is such that the cup-shaped element is subjected to a predetermined axial elastic preloading: i.e., the peripheral edge 8a is kept elastically pressed in seal contact against the annular valve seat with conical surface 12 under the axial thrust exerted by the side wall 9, as well as under the consequent component of radial thrust applied by the end wall 8 of the cup-shaped element 7 thanks to the conical conformation of the valve seat 11. This condition corresponds, as has been said, to the normally closed position of the check valve 6 according to the invention, in which the flow from the passage downstream 5 to the passage upstream 4 is prevented in a reliable and safe way.

When within the passage upstream 4 an overpressure is set up of an amount higher than a pre-set threshold value, the check valve 6 passes promptly from the closing condition to the opening condition following upon deflection, i.e., the axial displacement of the end wall 8 of the cup-shaped element 7 in the direction of the second tubular element 3. Said displacement causes an elastic return of the circumferencial edge 8a and a consequent radial contraction thereof, which causes recession thereof in a radial-axial direction with respect to the valve seat 12. The valve 6 is thus opened so that the passage upstream 4 is set in communication with the passage downstream 5 through the axial channels 16 and the radial channels 15 set below the free edge 9a of the side wall 9.

Contributing to the promptness of the elastic deformation of opening of the cup-shaped element 7 is the component of bending of the edge 9a within the sunken sectors 18 of the wall 14.

In fact, with respect to the case of the anti-siphon valve according to the already mentioned European patent No. EP-B-1 093 828, the albeit partial resting of the free edge 9a of the side wall 9 causes the higher elastic yielding of the latter to enable opening of the valve 6 with values of pressure applied to the end wall 8 not only generally corresponding to the ones for a normal check valve for medical uses (typically between 0.005 and 0.02 bar), but even with considerably lower values.

This ensures that the check valve according to the invention will have a surprising promptness and immediacy of opening.

It should also be noted that opening of the valve 6 following upon axial-radial displacement of the circumferencial edge 8a of the end wall 8, in addition to ensuring prompt and immediate opening of the valve 6, reduces any risk of undesirable adhesion between the edge 8a and the valve seat 12, also following upon prolonged periods of closing of the valve, which could jeopardize correct opening thereof.

In the opening condition of the valve 6, as the flowrate of fluid within the inlet passage 4 increases, a proportionally greater deflection (or axial displacement) of the end wall 8 of the cup-shaped element 7 occurs, and consequently a proportionally greater widening of the passage between the circumferencial edge 8a and the conical surface 16: the loss of head through the valve 6 is consequently approximately linear.

The axial projections 19 of the two raised sectors 17 have the function of arrests, designed to prevent the end wall 8, in a condition of complete opening of the valve 6, from possibly obstructing the outlet passage 5.

Return into the closing position of the check valve 6, as soon as the pressure balance between the passage upstream 4 and the passage downstream 5 is restored or else in the case of overpressure in the passage downstream 5, is brought about as a result of the immediate return of the end wall 8 into the resting configuration of the corresponding peripheral edge 8a against the annular valve seat 12.

Of course, the details of construction and the embodiments may vary widely with respect to what is described and illustrated herein, without thereby departing from the scope of the present invention, as defined in the ensuing claims.

What is claimed is:

1. A one-way valve for medical infusion lines comprising:
a first tubular element and a second tubular element, which define, respectively, a passage upstream and a passage downstream which are coaxial to one another and transversely set between which is a diaphragm made of elastically deformable material co-operating in a fluid-tight way with an annular valve seat of said first tubular element to keep said valve normally closed,
wherein a predetermined pressure of fluid in said passage upstream brings about a displacement or an elastic deformation of said diaphragm and consequent opening of said valve;
said annular valve seat defined by a wall with a conical surface of said first tubular element diverging towards said second tubular element;
said diaphragm comprising an end wall of a cup-shaped element having an outer peripheral edge, said outer edge normally pressed in sealed contact against said annular valve seat under an axial thrust exerted by a side wall of said cup-shaped element wherein a deflection or an axial displacement of said end wall of the cup-shaped element is brought about in use by said predetermined pressure of fluid determining a radial contraction of said outer peripheral edge and a consequent separation of said outer edge from said annular valve seat wherein said side wall of the cup-shaped element has a free edge resting against a grooved transverse surface of said second tubular element communicating with said passage downstream;
said grooved transverse surface having a plurality of radial channels, said radial channels alternately angularly separated from each other by raised angular resting portions and sunken angular non-resting portions, said free edge of the side wall of said cup-shaped element being in contact only with said resting portions and avoiding contact with said non-resting portions, said sunken angular non-resting portions extending further toward said diaphragm than said plurality of channels extends toward said diaphragm and less than said resting portions extend toward said diaphragm.

2. The valve according to claim 1, wherein said grooved transverse surface has an array of radial channels each of which is prolonged in a respective axial channel formed in said second tubular element at the side of said side wall of the cup-shaped element, said radial channels being separated by sectors alternatively raised and sunken.

3. The valve according to claim 2, wherein at least part of said sectors are formed with axial projections projecting towards said end wall of said cup-shaped element.

4. The valve according to claim 1, wherein said end wall of the cup-shaped element has a variable thickness, increasing towards a central part of said end wall.

5. The valve according to claim 1, wherein said side wall of the cup-shaped element has a variable thickness, increasing towards said free edge.

6. The valve according to claim 1, wherein said peripheral edge of the end wall of said cup-shaped element has a minimum thickness.

7. The valve according to claim 1, wherein said first tubular element has a transverse wall facing said end wall of said cup-shaped element formed with an array of radial passages communicating with said passage upstream.

8. The valve according to claim 1, wherein said free edge of the side wall of said cup-shaped element has an external annular groove.

9. The valve according to claim 1, wherein said cup-shaped element is made of a single piece of injection-moulded soft elastomeric material.

10. The valve according to claim 9 where said elastomeric material comprises liquid silicone.

11. The valve according to claim 1, wherein said first and second tubular elements are pre-arranged for tube-tube connections, or else luer-tube connections or else tube-luer connections, or else luer-luer connections, of a medical line.

12. The valve of claim 1 wherein said plurality of radial channels is separate from said plurality of sunken non-resting portions.

13. The valve of claim 1 wherein each channel of said plurality of radial channels is bounded on opposite radial sides by a non-resting portion of said plurality of sunken non-resting portions and a raised resting portion of said plurality of raised resting portions.

14. A one-way valve for medical infusion lines comprising:
a first tubular element and a second tubular element, which define, respectively, a passage upstream and a passage downstream which are coaxial to one another and transversely set between which is a diaphragm made of elastically deformable material co-operating in a fluid-tight way with an annular valve seat of said first tubular element to keep said valve normally closed,
wherein a predetermined pressure of fluid in said passage upstream brings about a displacement or an elastic deformation of said diaphragm and consequent opening of said valve;
said annular valve seat defined by a wall with a conical surface of said first tubular element diverging towards said second tubular element;
said diaphragm comprising an end wall of a cup-shaped element having an outer peripheral edge, said outer edge normally pressed in sealed contact against said annular valve seat under an axial thrust exerted by a side wall of said cup-shaped element wherein a deflection or an axial displacement of said end wall of the cup-shaped element is brought about in use by said predetermined pressure of fluid determining a radial contraction of said outer peripheral edge and a consequent separation of said outer edge from said annular valve seat wherein said side wall of the cup-shaped element has a free edge resting against a grooved transverse surface of said second tubular element communicating with said passage downstream;
said grooved transverse surface having a plurality of radial channels, each radial channel of said radial channels extending radially and bounded on opposite sides by an angular resting portion and a sunken angular non-resting portion, said free edge of the side wall of said cup-shaped element being in contact only with said resting portion and avoiding contact with said non-resting portion.

15. The valve of claim 14 wherein said resting surface extends further toward said diaphragm than said sunken portion extends toward said diaphragm to allow said diaphragm to contact said resting surface.

16. The valve of claim 14 wherein said non-resting portion extends further toward said diaphragm than each channel extends toward said diaphragm.

* * * * *